(12) United States Patent
Attariwala et al.

(10) Patent No.: US 10,888,249 B2
(45) Date of Patent: Jan. 12, 2021

(54) CANNABIS DRUG DETECTION DEVICE

(71) Applicant: Cannabix Breathalyzer Inc., Delta (CA)

(72) Inventors: Rajpaul Attariwala, Vancouver (CA); Kulwant Malhi, Delta (CA)

(73) Assignee: Cannabix Technologies Inc., Burnaby (CA)

( * ) Notice: Subject to any disclaimer, the term of this patent is extended or adjusted under 35 U.S.C. 154(b) by 22 days.

(21) Appl. No.: 14/689,434

(22) Filed: Apr. 17, 2015

(65) Prior Publication Data

US 2015/0305651 A1    Oct. 29, 2015

Related U.S. Application Data

(60) Provisional application No. 61/981,650, filed on Apr. 18, 2014.

(51) Int. Cl.
| | | |
|---|---|---|
| *A61B 5/08* | (2006.01) | |
| *A61B 5/087* | (2006.01) | |
| *A61B 5/097* | (2006.01) | |
| *A61B 5/00* | (2006.01) | |

(52) U.S. Cl.
CPC .............. *A61B 5/082* (2013.01); *A61B 5/087* (2013.01); *A61B 5/097* (2013.01); *A61B 5/4845* (2013.01)

(58) Field of Classification Search
CPC ......... A61B 5/082; A61B 5/087; A61B 5/097; A61B 5/4845
See application file for complete search history.

(56) References Cited

U.S. PATENT DOCUMENTS

| | | | |
|---|---|---|---|
| 5,361,771 A * | 11/1994 | Craine ................ | A61B 5/0813 600/473 |
| 5,871,905 A | 2/1999 | Thieme et al. | |
| 7,285,246 B1 * | 10/2007 | Martin ................ | A61B 5/097 422/408 |
| 8,237,118 B2 | 8/2012 | Prox et al. | |
| (Continued) | | | |

FOREIGN PATENT DOCUMENTS

WO     2012/120140 A1     9/2012

OTHER PUBLICATIONS

Balbino et al., A Comparative Study Between Two Different Conventional Working Electrodes for Detection of Tetrahydrocannabinol Using Square-Wave Voltammetry: a New Sensitive Method for Forensic Analysis, J. Braz. Chem. Soc., 2014, pp. 589-596, vol. 25, No. 3.

(Continued)

*Primary Examiner* — David Z Huang
(74) *Attorney, Agent, or Firm* — Oyen Wiggs Gree

(57) ABSTRACT

A system for collecting cannabis and the psychoactive component tetrahydrocannabinol from a sample of exhaled breath is disclosed. Single or multiple exhaled breaths are conditioned by removing contaminants, and regulating flow rate and/or pressure to collect a sample of tetrahydrocannabinol for timely local or remote analysis. The cannabis detection system comprises a containment trap for removing interfering materials from the breath of the subject and a collection component for sampling components of breath introduced into the system through the containment trap for analysis to determine a presence of THC in the breath.

20 Claims, 1 Drawing Sheet

(56) References Cited

U.S. PATENT DOCUMENTS

| | | | |
|---|---|---|---|
| 8,485,984 B2 | 7/2013 | Giron et al. | |
| 9,709,581 B1 | 7/2017 | Gordon | |
| 2005/0085740 A1 | 4/2005 | Davis et al. | |
| 2005/0161597 A1 | 7/2005 | Guevremont et al. | |
| 2006/0078467 A1* | 4/2006 | Stock | G01N 33/0006 |
| | | | 422/84 |
| 2007/0239069 A1 | 10/2007 | Guirguis | |
| 2008/0035143 A1* | 2/2008 | Sievers | A61K 9/0075 |
| | | | 128/203.12 |
| 2008/0056946 A1 | 3/2008 | Ahmad | |
| 2008/0183388 A1 | 7/2008 | Goodrich | |
| 2009/0017555 A1* | 1/2009 | Jehanli | G01N 33/50 |
| | | | 436/501 |
| 2009/0170072 A1 | 7/2009 | Mink et al. | |
| 2011/0144535 A1 | 6/2011 | Guirguis | |
| 2011/0178420 A1 | 7/2011 | Ridder et al. | |
| 2011/0270053 A1 | 11/2011 | Utley et al. | |
| 2012/0302907 A1 | 11/2012 | Beck | |
| 2013/0006068 A1* | 1/2013 | Gemer | A61B 10/0051 |
| | | | 600/314 |
| 2013/0021153 A1 | 1/2013 | Keays | |
| 2013/0066223 A1 | 3/2013 | Beck et al. | |
| 2014/0094391 A1 | 4/2014 | McDevitt et al. | |
| 2014/0276100 A1 | 9/2014 | Satterfield et al. | |
| 2014/0288454 A1 | 9/2014 | Paz et al. | |
| 2014/0311215 A1 | 10/2014 | Keays et al. | |
| 2014/0366609 A1* | 12/2014 | Beck | A61B 5/082 |
| | | | 73/23.3 |
| 2015/0305651 A1 | 10/2015 | Attariwala | |
| 2016/0022946 A1* | 1/2016 | Sislian | G01N 1/2202 |
| | | | 600/543 |
| 2016/0089058 A1* | 3/2016 | Hyohgo | A61B 5/087 |
| | | | 600/538 |
| 2017/0023453 A1 | 1/2017 | Hill, Jr. et al. | |
| 2017/0119279 A1 | 5/2017 | Ahmad et al. | |
| 2019/0307396 A1 | 10/2019 | Attariwala et al. | |

OTHER PUBLICATIONS

Beck et al., Detection of drugs of abuse in exhaled breath using a device for rapid collection: comparison with plasma, urine and self-reporting in 47 drug users, IOP Science, Journal of Breath Research, 2013, 2 pages, vol. 7, No. 2, http://iopscience.iop.org/1752-7163/7/2/026006/.

Cusack et al., Report on Roadside Drug Testing and Equipment and Related Matters, Medical Bureau of Road Safety, Jun. 2012, 88 pages, http://www.drugsandalcohol.ie/18630/1/MBRS_Roadside_Drug_Testing_Report_2012.pdf.

Dees, New technology to help in roadside drug testing, PoliceOne.com News, Sep. 26, 2010, 2 pages, http://www.policeone.com/police-products/police-technology/articles/2835269-New-technology-to-help-in-roadside-drug-testing/.

Downs, Are Roadside Cannabis Breathalyzer Tests Around the Corner?, Alternet, Dec. 8, 2013, 4 pages, http://www.alternet.org/drugs/are-roadside-cannabis-breathalyzer-tests-around-corner?paging=off&current_page=1#bookmark.

Gelfand, Device Offers a Roadside Dope Test, MIT Technology Review, Aug. 4, 2009, 2 pages, vol. 1.13.05.10.

IOP, Breath Study brings roadside drug testing closer, Phys Org, Apr. 25, 2013, 2 pages, http://phys.org/news/2013-04-roadside-drug-closer.html.

IOP, Breath Study brings roadside drug testing closer, ScienceDaily, Apr. 25, 2013, 2 pages, http://www.sciencedaily.com/releases/2013/04/130425213901.htm.

Maxwell et al., Paper-based electroanalytical devices for accessible diagnostic testing, MRS Bulletin, Apr. 2013, pp. 309-314, vol. 38.

Newsquest Media Group, Police force becomes first to 'breathalyse' suspected drug-drivers at roadside, The Northern Echo, Dec. 2, 2013, 1 page, http://www.thenorthernecho.co.uk/news/local/northyorkshire/10849904.Police_force_becomes_first_to__breathalyse__suspected_drug_drivers_at_roadside/.

Pamer, LAPD Highlights New Roadside Swab Drug Test, KTLA5, Dec. 27, 2013, 2 pages, http://ktla.com/2013/12/27/lapd-highlights-new-roadside-swab-drug-test/#axzz2ySflPbix.

Pathtech, Inc., Science, Drug Testing, Forensic Products, 2015, 7 pages, http://www.pathtech.com.au/.

Pathtech, Science Archives, Drug Testing—Saliva Testing products, 2015, 6 pages, http://www.pathtech.com.au/pathtech-product-details?ProductID=0U143U2L980S8W7844573E641R8D&MainCatergory=Drug%20And%20Alcohol%20Testing&Agency=Drug%20Testing&ProductCategory=Saliva%A0Testing.

Smith, Scientists Develop Breathalyzer That Can 'Smell' Drugs, red Orbit, Apr. 26, 2013, 2 pages, http://www.redorbit.com/news/health/1112832161/breathalyzer-tests-for-drugs-alcohol-breath-cocaine-amphetamines-marijuana-042613/.

Softpedia, Portable Drug Test Devices to Hit the Market Soon, Sep. 22, 2010, 3 pages, http://news.softpedia.com/news/Portable-Drug-Test-Devices-to-Hit-the-Market-Soon-157515.shtml.

U.S. Department of Transportation, Pilot Test of New Roadside Survey Methodology for Impaired Driving, Jan. 2007, 104 pages, DOT HS 810 704.

* cited by examiner

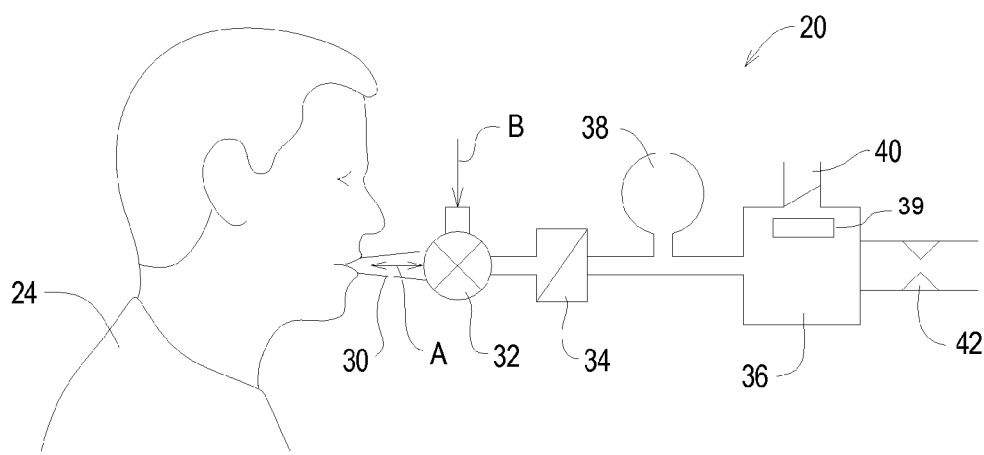
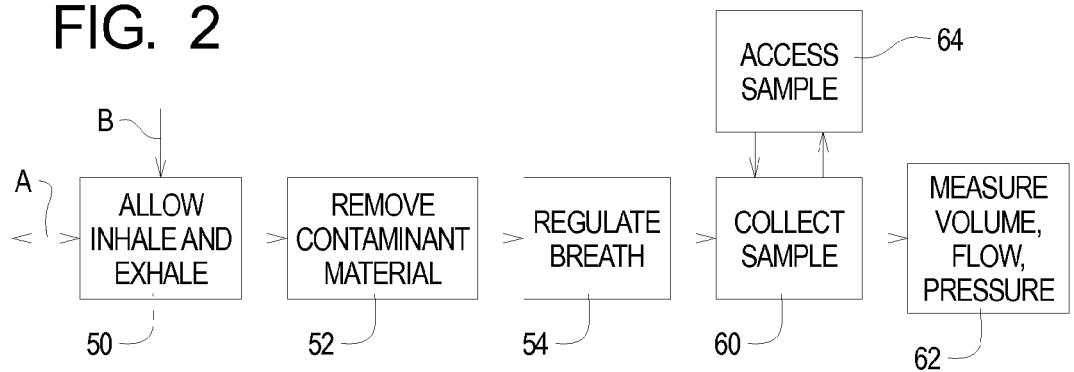

CANNABIS DRUG DETECTION DEVICE

RELATED APPLICATION

This application claims benefit of U.S. Provisional Application Ser. No. 61/981,650 filed Apr. 18, 2014, which is incorporated by reference herein in its entirety.

TECHNICAL FIELD

The present invention is directed to a portable or fixed device for the detection of cannabis, specifically tetrahydrocannabinol (THC), from the exhaled breath of a subject.

RELATED ART

Detection of cannabis is commonly performed by urine, blood, or oral specimen sampling. These methods are frequently invasive and require complicated devices for analysis. Alcohol is a simple molecule which can be examined directly by an exhaled breath exam, most commonly by exhaling into an ion spectroscopy chamber. This method has proven reliable and is accepted by legal systems as a noninvasive method to quantify alcohol levels.

Detection of drugs by an exhaled breath method has been proposed; however, the technique proposed is generic for multiple different illicit drugs. The proposed devices have been described for detection of drugs within the exhaled breath using a fluid collection or filtration system. Most of these devices describe a tube into which the subject exhales, which indiscriminately collects molecules of interest in either a liquid or filtration device. This liquid or fluid trapped within a filter is then sent to a laboratory for analysis, which may take several days. These devices lack methods for measurement of exhaled breath volumetric flowrate and for regulating pressure. With exhaled breath, each individual has the capability to exhale to different pressures, and if, for example, a filter based system is utilized to measure cannabis, an unregulated high pressure provided by a subject can tear apart the filter. Also, as each subject has a different amount of exhaled breath, it is important to be able to quantify the flowrate, or total volumetric flow, that has been breathed into the device.

The prior art devices which are designed to measure exhaled breath describe a mouthpiece which comprises a tube into which the subject exhales. This tube, without a rebreather valve, requires that the subject inhale through their nose, or remove the device from their lips to inhale.

Prior devices designed for exhaled breath do not describe a method of removal of fluid or solid contaminants, such as by way of a spit trap to collect or remove oral fluids, which prevents oral fluid contaminants from reaching a gas material detection chamber.

SUMMARY

The present invention comprises a system which is designed to measure a subject's breath, remove fluid and/or contaminants, and collect a tetrahydrocannabinol (THC) sample in an entrapment container for detection of cannabis use.

The invention includes a breathing tube with a rebreather valve, and a fluid and solid contaminant removal device. A pressure or volumetric flow measurement and regulating device is placed along the path of the exhaled breath pathway before or after a fixed or removable THC sample collecting chamber.

The THC collecting chamber may contain a port for cannabis sample detection, preparation or collection.

The described device is designed to permit detection of cannabis use relatively quickly, thus allowing it to be used, for example, by police officers in the field, etc.

BRIEF DESCRIPTION OF THE DRAWINGS

FIG. 1 is a schematic illustration showing an embodiment of the system to collect a cannabis sample from a breathing subject.

FIG. 2 is a flowchart illustrating a method for collecting a sample of cannabis.

REFERENCE NUMERALS IN THE DRAWINGS 20 device for cannabis detection
22 Method of materials movement for detection of THC and cannabis
24 Subject
30 mouthpiece
32 intake nonrebreather valve
34 contaminant trap
36 THC collection and housing component
38 pressure measurement and/or regulator
39 filter or sensor
40 liquid injection and or sampling port
42 volumetric flow measuring device
50 breathing device
52 contaminant removal
54 exhaled breath flow conditioner
60 THC collection device
62 volume, flow and pressure measurement device
64 sample preparation or collection device

DETAILED DESCRIPTION

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspects of the invention to the embodiments illustrated.

Cannabis detection by breath requires many components to separate raw cannabis and its metabolized forms from the psychoactive component tetrahydrocannabinol (THC).

The embodiment of the invention described in FIG. 1 consists of a portable cannabis detection system 20, where the psychoactive component of cannabis, tetrahydrocannabinol, is detected from the breath of a subject 24. FIG. 2 is the block diagram illustrating a method 22 for detecting and/or measuring THC in the breath of the subject 24. The method 22 depicted in the block diagram of FIG. 2 may be implemented by the portable cannabis detection system 20 of FIG. 1 or by any device or system capable of performing at least some combination of the steps described in FIG. 1.

The example portable cannabis detection system 20 comprises a mouthpiece 30, an intake non-rebreather valve 32, a contaminant trap 34, a THC collection and housing component 36, a pressure measurement and/or regulator component 38, a liquid injection/sampling port 40, and a volumetric flow measuring component 42. The cannabis detection system 20 is comprised of either disposable, or aseptic cleanable reusable components or as a single whole device.

The flowchart of FIG. 2 outlines the method for detection 22 of THC by outlining the direction materials pass through a device for cannabis detection such as the portable cannabis detection system 20 as generally described above. The detection method 22 depicted in FIG. 2 comprises the steps of providing a breathing device at block 50, removing contaminant material at block 52, conditioning the exhaled breath flow at block 54, collecting the THC at the block 60, measuring at least one and typically all of volume, flow, and pressure at block 62, and collecting or preparing a sample at block 64. The components and materials used by the steps in the flowchart of FIG. 2 are designed to provide to a THC collection device such as the THC collection component 36 of the example portable cannabis detection system 20 described above, at block 60, an appropriate sample of exhaled breath from which THC content may be detected and/or measured.

Referring now more specifically to FIG. 1 of the drawing, it can be seen that the example cannabis detection system 20 is coupled to the subject 24 via the mouthpiece 30. This mouthpiece 30 is directly connected to a non-rebreather valve 32 which allows the subject 24 to both inhale and exhale through the mouthpiece 30 without the subject 24 removing his lips from the mouthpiece 30 to inhale and without requiring the subject 24 to breathe through his nose to inhale. The air exchange step performed by the example mouthpiece 30 and non-rebreather valve 32 is described at the block 50 in the flowchart of FIG. 2. Arrows A and B in FIGS. 1 and 2 show air entering and exiting the system, respectively, thereby allowing the subject 24 to inhale and exhale through the mouthpiece 30, with the exhaled breath being redirected into the contaminant trap 34.

The example contaminant trap 34 consists of a device that allows interfering materials, such as vapor, fluid, and/or solids, to be removed from the exhaled breath from the subject 24 and allows exhaled THC-containing breath to pass through unrestricted. The example trap 34 thus removes contaminants from the exhaled breath as performed by the removing contaminant material step shown at block 52 in FIG. 2. The containment trap 34 can be removed to access liquid contaminants which may include metabolized or unmetabolized components of cannabis or to remove components of exhaled breath that would interfere with the detection of THC in the collection device 36. The example containment trap 34 may be a contaminant removal component comprising a flap valve covering holes that allows oral fluid to pass out of the device or to be collected in another chamber.

The degree of effort of exhalation by subjects such as the subject 24 is variable, which results in the exhaled breath occurring at various pressures. To provide the THC collection component 36 with a suitable pressure or flow rate, a pressure regulator and or measuring device 38 is placed in line with the exhaled breath. The example THC collection component 36 prepares the exhaled breath to be appropriately collected as shown at the step corresponding to block 54 in the flowchart of FIG. 2. The pressure measuring and/or regulating component 38 can be placed anywhere beyond the mouthpiece to control pressure input into or from the device. A wide variety of pressure regulating or measuring devices can be utilized, and an example may consist of a balloon which expands with high pressure exhaled breath, and collapses to deliver exhaled breath to the detection component of the device at a controlled pressure.

The THC collection component 36 may consist of a vacuum, gas and/or liquid filled chamber with a filter or sensor 39 that is capable of collecting or detecting THC. The example THC collection device 36 may be directly accessed by a sampling port 40 for either sampling or filling with gas or liquid materials as shown by block 64 in FIG. 2. The THC collection component 36 in whole or in part may be removed from the cannabis detection system 20. An embodiment of the THC collection component 36 would be a filter or cartridge that can be removed for sampling via high performance liquid chromatography and/or mass spectrometry. Other potential embodiments include an ion or magnetic resonance chamber, color detection, light spectroscopy, and/or nanoparticle filter. In another embodiment, the THC collection component 36 may consist of a chemical that forms an appearance change material which reacts with THC. This would result in a reaction or change in chemical or physical properties of such chemical so that the alteration would be detectable. For example, a chemical coming into contact with THC could result in a changing of color of the chemical. This color change can then be visualized by detection/looking through the access port 40. The port 40 can be used to prepare the filtered sample for any of these methods.

In line with the exhaled breath flowchart as outlined in FIG. 1, a volumetric flow measuring device 42 is placed to quantify the amount of exhaled breath provided by the subject 24. The location of this measurement device 62 as shown in the flowchart of FIG. 2 can be placed anywhere along the pathway of the exhaled breath, or may be coupled with the step of conditioning the exhaled breath flow shown by block 54 and/or the pressure measurement or regulator device 38. The purpose for recording the volume of breath passing through the device is to enable a way to measure how much exhaled breath has been input into the system 20. Each individual, based on their lung capacity and/or effort, can exhale different volumes. A volumetric flow rate measurement device incorporated into the system for cannabis detection provides a means to quantify this amount per breath, and/or as a total sum during use of the device. This ensures that sufficient exhaled breath is delivered to the THC collection component 36 to allow detection of cannabis or THC use. A variety of different flow meters can be used as the volumetric flow measuring device 42. One example is a rotating blade which spins with exhaled breath and records the volume of flow that is exhaled. A second example would be a diaphragm that detects air pressure and converts air pressure to flow volume.

In one embodiment, the device can provide results of THC detection in seconds or minutes based on how the cannabis detection device 20 and/or THC collection analysis method 22 are implemented.

In another embodiment, the device can be implemented or equipped to correlate a measured or detected THC sample to a specific subject. For example, a DNA fingerprint method can be added to the contaminant trap 34, or elsewhere inline, to detect and/or monitor who is utilizing the device (e.g., through use of the subject's saliva or other DNA sample). In this case, the THC sample measurement and the DNA sample are stored together and/or cross-reference in a way that ensures that a particular THC sample measurement and DNA sample are positively associated with each other for evidentiary purposes if necessary.

Several embodiments of the invention have been described. It should be understood that the concepts described in connection with one embodiment of the invention may be combined with the concepts described in connection with another embodiment (or other embodiments) of the invention.

While an effort has been made to describe some alternatives to the preferred embodiment, other alternatives will readily come to mind to those skilled in the art. Therefore, it should be understood that the invention may be embodied in other specific forms without departing from the spirit or central characteristics thereof. The present examples and embodiments, therefore, are to be considered in all respects as illustrative and not restrictive, and the invention is not intended to be limited to the details given herein.

What is claimed is:

1. A single-device cannabis detection system for detecting THC in a breath of a subject, comprising:
   a housing defining the single-device cannabis detection system;
   a mouthpiece in fluid communication with the housing for facilitating introduction of the breath into the system by the subject;
   a containment trap associated with the housing for removing interfering materials including oral fluids from the breath of the subject;
   a non-rebreather valve positioned downstream of the mouthpiece and upstream of the containment trap, the non-rebreather valve in fluid communication with the mouthpiece, the containment trap and ambient air, the non-rebreather valve operative to direct ambient air entering the non-rebreather valve upstream through the mouthpiece without flowing through the containment trap when the subject inhales through the mouthpiece and to direct the breath of the subject downstream to the containment trap when the subject exhales through the mouthpiece; and
   a collection component within the housing positioned downstream of the containment trap for sampling components of breath introduced into the system through the containment trap for analysis to determine a presence of THC in the breath.

2. A cannabis detection system as recited in claim 1, further comprising means for correlating a measured or detected THC sample to a specific subject.

3. A cannabis detection system as recited in claim 1 wherein the collection component comprises a sensor capable of detecting THC.

4. A cannabis detection system as recited in claim 1, further comprising a sampling port in the housing for allowing access to the components sampled by the collection component.

5. A cannabis detection system as recited in claim 1, in which the collection component further comprises a filter for trapping components of the breath sampled by the collection component.

6. A cannabis detection system as recited in claim 1, in which the containment trap comprises a flap valve covering holes to allow the oral fluids to be removed from the breath introduced into the system.

7. A cannabis detection system as recited in claim 1 comprising a pressure regulator for regulating the pressure of the breath introduced into the collection component, the pressure regulator being positioned upstream of the collection component and configured to supply the breath to the collection component, in which the pressure regulator comprises a balloon that inflates to regulate the pressure of breath introduced into the collection component.

8. A cannabis detection system as recited in claim 7, wherein the pressure regulator is configured to measure the pressure of the breath.

9. A cannabis detection system as recited in claim 1, in which the components of the breath sampled by the collection component are analyzed using at least one of a liquid chromatography sensor, a mass spectrometry sensor, an ion resonance chamber, a magnetic resonance chamber, a light spectroscopy sensor, an appearance change material enabling visual detection of THC, or a nanoparticle filter.

10. A cannabis detection system as recited in claim 9, wherein the appearance change material comprises a material that changes color when in contact with THC, and wherein the appearance change material is visible through an access port in the housing.

11. A method of detecting cannabis use by analyzing a breath of a subject using a single-device cannabis detection system having a housing, the method comprising the steps of:
   introducing the breath into the system through a mouthpiece in fluid communication with the housing;
   providing a non-rebreather valve located downstream of the mouthpiece and upstream of a containment trap associated with the housing to allow the subject to inhale and exhale through the mouthpiece while introducing breath into the system;
   removing contaminant material from the breath using the containment trap associated with the housing, the contaminant material including oral fluids, the non-rebreather valve in fluid communication with the mouthpiece, the containment trap and ambient air, the non-rebreather valve operative to direct ambient air entering the non-rebreather valve upstream through the mouthpiece without flowing through the containment trap when the subject inhales through the mouthpiece and to direct the breath of the subject downstream to the containment trap when the subject exhales through the mouthpiece;
   collecting with a collection component positioned within the housing downstream of the containment trap a sample of at least one component of the breath of the subject after the contaminant material has been removed therefrom; and
   analyzing the sample for the presence of THC.

12. A method as recited in claim 11, wherein analyzing the sample for the presence of THC comprises the step of using a sensor capable of detecting THC, the sensor being provided as part of the collection component.

13. A method as recited in claim 11, further comprising the step of measuring a volumetric amount of breath introduced into the system by the subject.

14. A method as defined in claim 11, wherein, prior to said analyzing step, the sample is prepared for said analyzing step by accessing the sample through a port provided in the housing.

15. A single-device cannabis detection system for detecting THC in a breath of a subject, comprising:
   a housing defining the single-device cannabis detection system;
   a mouthpiece in fluid communication with the housing for facilitating introduction of the breath into the system by the subject;
   a containment trap associated with the housing and positioned downstream of the mouthpiece for removing interfering materials including oral fluids from the breath of the subject introduced into the system;
   a non-rebreather valve positioned downstream of the mouthpiece and upstream of the containment trap, the non-rebreather valve in fluid communication with the mouthpiece, the containment trap and ambient air, the non-rebreather valve operative to direct ambient air entering the non-rebreather valve upstream through the mouthpiece without flowing through the containment trap when the subject inhales through the mouthpiece and to direct the breath of the subject downstream to the containment trap when the subject exhales through the mouthpiece;

a flow measurement device associated with the housing and positioned downstream of the mouthpiece for measuring a volumetric amount of breath introduced into the system by the subject;

a collection component within the housing for sampling components of breath introduced into the system through the containment trap for analysis to determine a presence of THC in the breath; and a pressure regulator for regulating the pressure of the breath introduced into the system, the pressure regulator being positioned upstream of the collection component and configured to supply the breath to the collection component.

16. A cannabis detection system as recited in claim 15, in which the collection component further comprises a filter for trapping components of the breath sampled by the collection component.

17. A cannabis detection system as recited in claim 15, in which the containment trap comprises a flap valve covering holes to allow the oral fluids to be removed from the breath introduced into the system.

18. A cannabis detection system as recited in claim 15, in which the pressure regulator comprises a balloon that inflates to regulate the pressure of breath introduced into the pressure regulator.

19. A cannabis detection system as recited in claim 15, in which the components of the breath sampled by the collection component are analyzed using at least one of a liquid chromatography sensor, a mass spectrometry sensor, an ion resonance chamber, a magnetic resonance chamber, a light spectroscopy sensor, an appearance change material that changes appearance when in contact with THC, or a nanoparticle filter.

20. A cannabis detection system as recited in claim 19, wherein the appearance change material is visible through an access port in the housing.

* * * * *